(12) United States Patent
Cox

(10) Patent No.: US 7,331,972 B1
(45) Date of Patent: Feb. 19, 2008

(54) HEART VALVE CHORD CUTTER

(75) Inventor: Daniel L. Cox, Palo Alto, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 573 days.

(21) Appl. No.: 10/295,383

(22) Filed: Nov. 15, 2002

(51) Int. Cl.
*A61B 17/32* (2006.01)

(52) U.S. Cl. ..................................... 606/170

(58) Field of Classification Search ............... 606/167, 606/159, 170
See application file for complete search history.

(56) References Cited

U.S. PATENT DOCUMENTS

| | | | |
|---|---|---|---|
| 3,716,058 A | 2/1973 | Tanner et al. |
| 4,719,924 A | 1/1988 | Crittenden et al. |
| 4,781,186 A | 11/1988 | Simpson et al. |
| 4,830,023 A | 5/1989 | de Toledo et al. |
| 4,920,980 A | 5/1990 | Jackowski |
| 4,994,067 A | 2/1991 | Summers |
| 5,040,548 A | 8/1991 | Yock |
| 5,061,273 A | 10/1991 | Yock |
| 5,100,418 A | 3/1992 | Yoon et al. |
| 5,171,233 A | 12/1992 | Amplatz et al. |
| 5,234,443 A | 8/1993 | Phan et al. |
| 5,242,456 A | 9/1993 | Nash et al. |
| 5,350,395 A | 9/1994 | Yock |
| 5,358,479 A | 10/1994 | Wilson |
| 5,383,260 A | 1/1995 | Deschenes et al. |
| 5,431,673 A | 7/1995 | Summers et al. |
| 5,441,483 A | 8/1995 | Avitall |
| 5,451,233 A | 9/1995 | Yock |
| 5,487,757 A | 1/1996 | Truckai et al. |
| 5,495,974 A | 3/1996 | Deschenes et al. |
| 5,518,162 A | 5/1996 | Deschenes et al. |
| 5,522,873 A | 6/1996 | Jackman et al. |
| 5,531,686 A | 7/1996 | Lundquist et al. |
| 5,554,184 A | 9/1996 | Machiraju |
| 5,569,277 A | 10/1996 | Evans et al. |
| 5,571,215 A | 11/1996 | Sterman et al. |
| 5,609,598 A | 3/1997 | Laufer et al. |
| 5,613,937 A | 3/1997 | Garrison et al. |
| 5,617,854 A | 4/1997 | Munsif |

(Continued)

FOREIGN PATENT DOCUMENTS

DE 10161543 A1 6/2003

(Continued)

OTHER PUBLICATIONS

Messas, et al., *Chordal Cutting A New Therapeutic Appr;oach for Ischmic Mitral Regurgitaion*, 2001 American Heart Association Inc., pp. 1958-1963.

(Continued)

*Primary Examiner*—(Jackie) Tan-Uyen Ho
*Assistant Examiner*—Melanie Tyson
(74) *Attorney, Agent, or Firm*—Blakely, Sokoloff, Taylor & Zafman LLP

(57) ABSTRACT

A medical device and method for percutaneously treating a heart valve. In one embodiment, the medical device includes a catheter having a proximal portion, a distal portion, and a notch formed near the distal portion. A cutting element may be disposed within the distal portion and is moveable across the notch to slice through a heart chord.

22 Claims, 16 Drawing Sheets

U.S. PATENT DOCUMENTS

| | | |
|---|---|---|
| 5,632,754 A | 5/1997 | Farley et al. |
| 5,640,955 A | 6/1997 | Ockuly et al. |
| 5,642,736 A | 7/1997 | Avitall |
| 5,681,280 A | 10/1997 | Rusk et al. |
| 5,681,346 A | 10/1997 | Orth et al. |
| 5,682,906 A | 11/1997 | Sterman et al. |
| 5,687,723 A | 11/1997 | Avitall |
| 5,728,129 A | 3/1998 | Summers |
| 5,782,828 A | 7/1998 | Chen et al. |
| 5,810,882 A | 9/1998 | Bolduc et al. |
| 5,823,955 A | 10/1998 | Kuck et al. |
| 5,824,008 A | 10/1998 | Bolduc et al. |
| 5,865,800 A | 2/1999 | Mirarchi et al. |
| 5,868,733 A | 2/1999 | Ockuly et al. |
| 5,868,767 A | 2/1999 | Farley et al. |
| 5,916,213 A | 6/1999 | Haissaguerre et al. |
| 5,961,440 A | 10/1999 | Schweich, Jr. et al. |
| 5,964,772 A | 10/1999 | Bolduc et al. |
| 5,972,022 A | 10/1999 | Huxel |
| 5,989,284 A | 11/1999 | Laufer |
| 6,001,095 A | 12/1999 | de la Rama et al. |
| 6,001,104 A | 12/1999 | Benderev et al. |
| 6,001,127 A | 12/1999 | Schoon et al. |
| 6,004,332 A | 12/1999 | Yoon et al. |
| 6,017,358 A | 1/2000 | Yoon et al. |
| 6,021,340 A | 2/2000 | Randolph et al. |
| 6,027,514 A * | 2/2000 | Stine et al. ................. 606/159 |
| 6,036,715 A | 3/2000 | Yock |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,090,096 A | 7/2000 | St. Goar et al. |
| 6,093,199 A | 7/2000 | Brown et al. |
| 6,110,100 A | 8/2000 | Talpade |
| 6,113,609 A | 9/2000 | Adams |
| 6,117,176 A | 9/2000 | Chen |
| 6,123,699 A | 9/2000 | Webster, Jr. |
| 6,149,669 A | 11/2000 | Li |
| 6,161,543 A | 12/2000 | Cox et al. |
| 6,162,168 A | 12/2000 | Schweich, Jr. et al. |
| 6,164,283 A | 12/2000 | Lesh |
| 6,165,119 A | 12/2000 | Schweich, Jr. et al. |
| 6,165,120 A | 12/2000 | Schweich, Jr. et al. |
| 6,165,164 A | 12/2000 | Hill et al. |
| 6,165,183 A | 12/2000 | Kuehn et al. |
| 6,165,197 A | 12/2000 | Yock |
| 6,174,323 B1 | 1/2001 | Biggs et al. |
| 6,178,346 B1 | 1/2001 | Amundson et al. |
| 6,182,664 B1 | 2/2001 | Cosgrove |
| 6,183,411 B1 | 2/2001 | Mortier et al. |
| 6,187,040 B1 | 2/2001 | Wright |
| 6,190,401 B1 | 2/2001 | Green et al. |
| 6,190,408 B1 | 2/2001 | Melvin |
| 6,203,531 B1 | 3/2001 | Ockuly et al. |
| 6,210,407 B1 | 4/2001 | Webster, Jr. |
| 6,210,432 B1 | 4/2001 | Solem et al. |
| 6,231,587 B1 | 5/2001 | Makower |
| 6,241,728 B1 | 6/2001 | Gaiser et al. |
| 6,254,568 B1 | 7/2001 | Ponzi |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,267,781 B1 | 7/2001 | Tu |
| 6,269,819 B1 | 8/2001 | Oz et al. |
| 6,270,526 B1 | 8/2001 | Cox |
| 6,283,127 B1 | 9/2001 | Sterman et al. |
| 6,283,962 B1 | 9/2001 | Tu et al. |
| 6,299,622 B1 | 10/2001 | Snow et al. |
| 6,312,447 B1 | 11/2001 | Grimes |
| 6,325,823 B1 | 12/2001 | Horzewski et al. |
| 6,355,030 B1 | 3/2002 | Aldrich et al. |
| 6,371,978 B1 | 4/2002 | Wilson |
| 6,374,476 B1 | 4/2002 | Ponzi et al. |
| 6,402,780 B2 | 6/2002 | Williamson, IV et al. |
| 6,402,781 B1 | 6/2002 | Langberg et al. |
| 6,408,214 B1 | 6/2002 | Williams et al. |
| 6,419,696 B1 | 7/2002 | Ortiz et al. |
| 6,461,366 B1 | 10/2002 | Seguin |
| 6,482,224 B1 | 11/2002 | Michler et al. |
| 6,488,689 B1 | 12/2002 | Kaplan et al. |
| 6,493,575 B1 | 12/2002 | Kesten et al. |
| 6,497,707 B1 | 12/2002 | Bowman et al. |
| 6,500,167 B1 | 12/2002 | Webster, Jr. |
| 6,537,198 B1 | 3/2003 | Vidlund et al. |
| 6,537,314 B2 | 3/2003 | Langberg et al. |
| 6,551,271 B2 | 4/2003 | Nguyen |
| 6,554,764 B1 | 4/2003 | Mueller et al. |
| 6,554,794 B1 | 4/2003 | Mueller et al. |
| 6,585,718 B2 | 7/2003 | Hayzelden et al. |
| 6,599,311 B1 | 7/2003 | Biggs et al. |
| 6,605,086 B2 | 8/2003 | Hayzelden et al. |
| 6,610,058 B2 | 8/2003 | Flores |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,638,286 B1 | 10/2003 | Burbank et al. |
| 6,638,289 B1 | 10/2003 | Burbank et al. |
| 6,648,903 B1 | 11/2003 | Pierson, III |
| 6,656,221 B2 | 12/2003 | Taylor et al. |
| 6,676,702 B2 | 1/2004 | Mathis |
| 6,706,065 B2 | 3/2004 | Langberg et al. |
| 6,709,442 B2 | 3/2004 | Miller et al. |
| 6,709,456 B2 | 3/2004 | Langberg et al. |
| 6,712,804 B2 | 3/2004 | Roue et al. |
| 6,718,985 B2 | 4/2004 | Hlavka et al. |
| 6,719,767 B1 | 4/2004 | Kimblad |
| 6,723,038 B1 | 4/2004 | Schroeder |
| 6,733,500 B2 | 5/2004 | Kelley et al. |
| 6,761,734 B2 | 7/2004 | Suhr |
| 6,764,510 B2 | 7/2004 | Vidlund et al. |
| 6,790,231 B2 | 9/2004 | Liddicoat et al. |
| 6,800,090 B2 | 10/2004 | Alferness et al. |
| 6,810,882 B2 | 11/2004 | Langberg |
| 6,824,562 B2 | 11/2004 | Mathis et al. |
| 6,852,124 B2 | 2/2005 | Cox et al. |
| 6,890,353 B2 | 5/2005 | Cohn et al. |
| 6,905,476 B2 | 6/2005 | Ponzi |
| 6,960,229 B2 | 11/2005 | Mathis et al. |
| 6,964,683 B2 | 11/2005 | Kowalsky et al. |
| 6,966,926 B2 | 11/2005 | Mathis |
| 6,989,028 B2 | 1/2006 | Lashinski et al. |
| 6,997,951 B2 | 2/2006 | Solem et al. |
| 2001/0003986 A1 | 6/2001 | Cosgrove |
| 2001/0005787 A1 | 6/2001 | Oz et al. |
| 2001/0018611 A1 | 8/2001 | Solem et al. |
| 2001/0027322 A1 | 10/2001 | Bowman |
| 2001/0044568 A1 | 11/2001 | Langberg et al. |
| 2002/0010483 A1 | 1/2002 | Folmer et al. |
| 2002/0010486 A1 | 1/2002 | Hirt |
| 2002/0013571 A1 | 1/2002 | Goldfarb et al. |
| 2002/0016628 A1 | 2/2002 | Langberg et al. |
| 2002/0026216 A1 | 2/2002 | Grimes |
| 2002/0035361 A1 | 3/2002 | Houser et al. |
| 2002/0042651 A1 | 4/2002 | Liddicoat et al. |
| 2002/0077647 A1 | 6/2002 | Snow et al. |
| 2002/0087169 A1 | 7/2002 | Brock et al. |
| 2002/0087173 A1 | 7/2002 | Alferness et al. |
| 2002/0103492 A1 | 8/2002 | Kaplan et al. |
| 2002/0103532 A1 | 8/2002 | Langberg et al. |
| 2002/0103533 A1 | 8/2002 | Langberg et al. |
| 2002/0111637 A1 | 8/2002 | Kaplan et al. |
| 2002/0161330 A1 | 10/2002 | Nguyen |

| | | | | | | | |
|---|---|---|---|---|---|---|---|
| 2002/0165484 | A1 | 11/2002 | Bowe et al. | WO | WO 99/30647 | A1 | 6/1999 |
| 2002/0165533 | A1 | 11/2002 | Flores | WO | WO 99/44534 | A1 | 9/1999 |
| 2002/0165534 | A1 | 11/2002 | Hayzelden et al. | WO | WO 00/03759 | | 1/2000 |
| 2002/0169502 | A1 | 11/2002 | Mathis | WO | WO 00/06026 | A2 | 2/2000 |
| 2002/0169504 | A1 | 11/2002 | Alferness et al. | WO | WO 00/06028 | A1 | 2/2000 |
| 2002/0183836 | A1 | 12/2002 | Liddicoat et al. | WO | WO 00/66027 | A2 | 2/2000 |
| 2002/0183837 | A1 | 12/2002 | Streeter et al. | WO | WO 00/16700 | A1 | 3/2000 |
| 2002/0183841 | A1 | 12/2002 | Cohn et al. | WO | WO 00/60995 | | 10/2000 |
| 2002/0188170 | A1 | 12/2002 | Santamore et al. | WO | WO 01/00111 | A1 | 1/2001 |
| 2003/0050598 | A1 | 3/2003 | Hayzelden et al. | WO | WO 01/00114 | A1 | 1/2001 |
| 2003/0069593 | A1 | 4/2003 | Tremulis et al. | WO | WO 01/26557 | A1 | 4/2001 |
| 2003/0078465 | A1 | 4/2003 | Pai et al. | WO | WO 01/28432 | A1 | 4/2001 |
| 2003/0083538 | A1 | 5/2003 | Adams et al. | WO | WO 01/28455 | A1 | 4/2001 |
| 2003/0093071 | A1 | 5/2003 | Hauck et al. | WO | WO 01/49213 | A2 | 7/2001 |
| 2003/0105520 | A1 | 6/2003 | Vidlund et al. | WO | WO 01/49213 | A3 | 7/2001 |
| 2003/0120340 | A1 | 6/2003 | Liska et al. | WO | WO 01/54618 | A1 | 8/2001 |
| 2003/0120341 | A1 | 6/2003 | Shennib et al. | WO | WO 01/89440 | A2 | 11/2001 |
| 2003/0144697 | A1 | 7/2003 | Mathis | WO | WO 02/00099 | A2 | 1/2002 |
| 2003/0144732 | A1 | 7/2003 | Cosgrove et al. | WO | WO 02/01999 | A2 | 1/2002 |
| 2003/0167071 | A1 | 9/2003 | Martin et al. | WO | WO 02/34167 | A2 | 5/2002 |
| 2003/0171776 | A1 | 9/2003 | Adams et al. | WO | WO 02/39925 | A2 | 5/2002 |
| 2003/0212453 | A1 | 11/2003 | Mathis et al. | WO | WO 02/053206 | A2 | 7/2002 |
| 2003/0216764 | A1 | 11/2003 | Tu et al. | WO | WO 02/060352 | | 8/2002 |
| 2004/0010231 | A1 | 1/2004 | Leonhardt et al. | WO | WO 02/062263 | A2 | 8/2002 |
| 2004/0044350 | A1 | 3/2004 | Martin et al. | WO | WO 02/062270 | A1 | 8/2002 |
| 2004/0044365 | A1 | 3/2004 | Bachman | WO | WO 02/062408 | A2 | 8/2002 |
| 2004/0049207 | A1 | 3/2004 | Goldfarb et al. | WO | WO 03/049619 | A2 | 6/2003 |
| 2004/0059531 | A1 | 3/2004 | Eigler et al. | WO | WO 03/073913 | A2 | 9/2003 |
| 2004/0098092 | A1 | 5/2004 | Butaric et al. | WO | WO 2004/012789 | A2 | 2/2004 |
| 2004/0138683 | A1 | 7/2004 | Shelton et al. | WO | WO 2004/014282 | A2 | 2/2004 |
| 2004/0138744 | A1 | 7/2004 | Lashinski et al. | | | | |
| 2004/0148020 | A1 | 7/2004 | Vidlund et al. | | | | |
| 2004/0153147 | A1 | 8/2004 | Mathis | | | | |
| 2005/0055089 | A1 | 3/2005 | Macoviack et al. | | | | |
| 2005/0267571 | A1 | 12/2005 | Spence et al. | | | | |
| 2005/0267573 | A9 | 12/2005 | Macoviak et al. | | | | |
| 2006/0041306 | A1 | 2/2006 | Vidlund et al. | | | | |
| 2006/0095025 | A1* | 5/2006 | Levine et al. .................. 606/15 | | | | |

FOREIGN PATENT DOCUMENTS

| | | |
|---|---|---|
| EP | 0377269 A1 | 7/1990 |
| WO | WO 98/29041 A1 | 7/1998 |
| WO | WO 99/00059 | 1/1999 |
| WO | WO 99/13777 | 3/1999 |

OTHER PUBLICATIONS

PCT Report for PCT International Patent Application PCT/US2004/031403, mailed Jun. 15, 2005. 5 pgs.

Bonow, Robert O., et al., "Guidelines for the Management of Patients with Valvular Health Diseases," Report of American College of Cardiology/American Heart Assoc. Task Force on Practice Guidelnes (Committee on Management of Pateints with Valvular Heart Disease), American College of Cardiology and American Heart Assoc., Inc., 1998, pp. 1949-1984.

PCT Invitation to Pay Additional fees for PCT International Appln. No. US03/36633, mailed May 19, 2004 (5 pages).

* cited by examiner

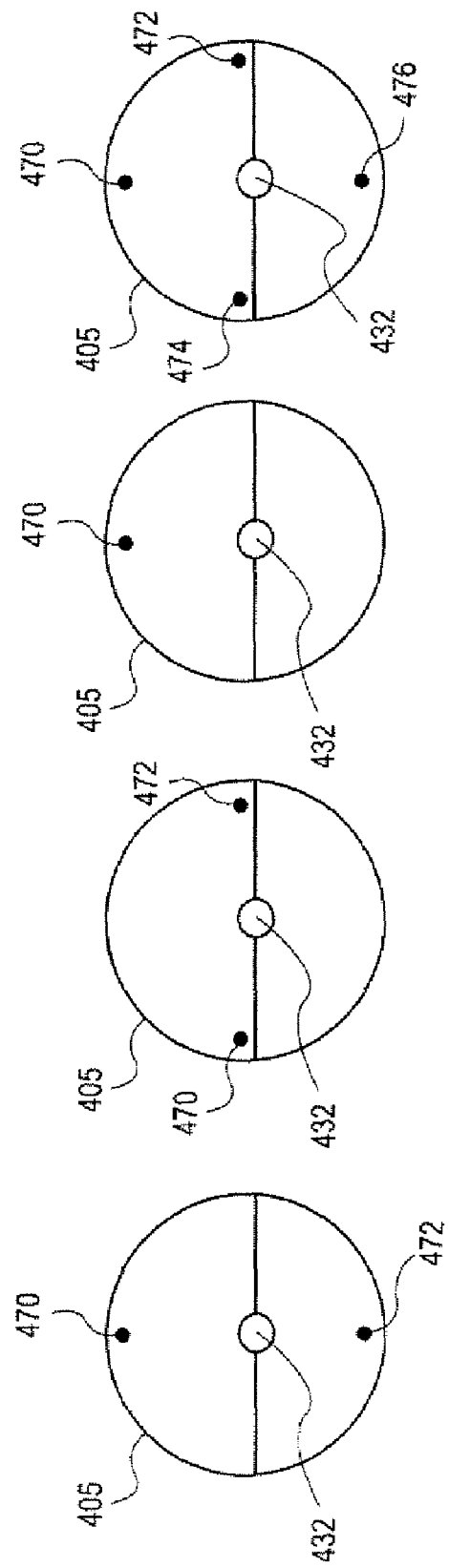

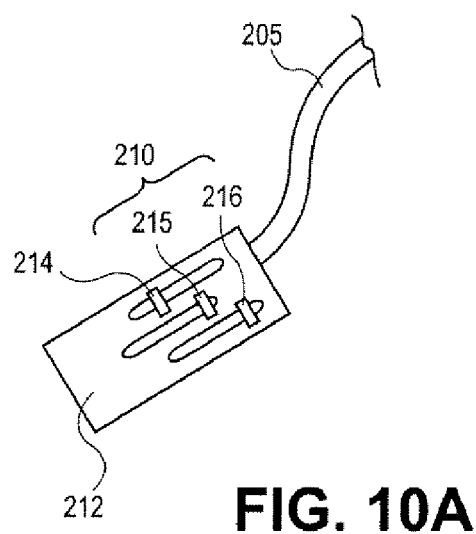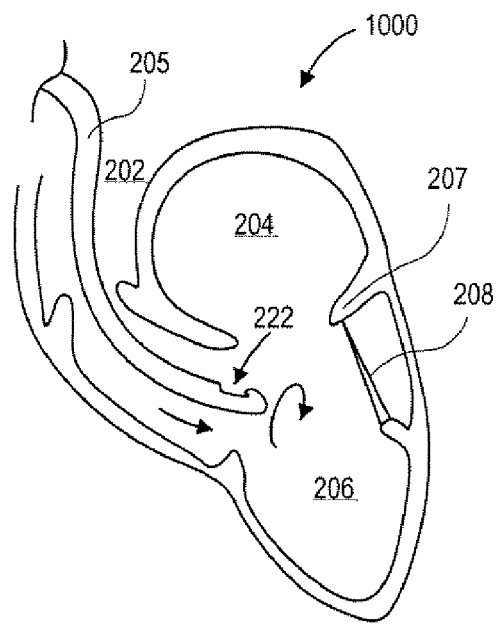
FIG. 10A
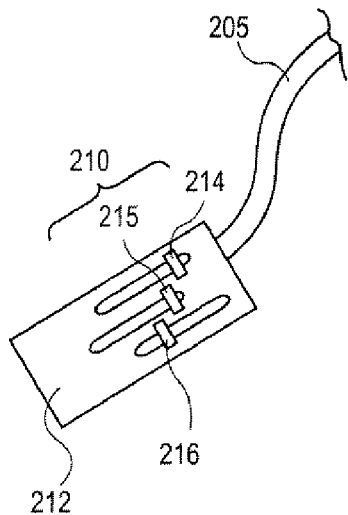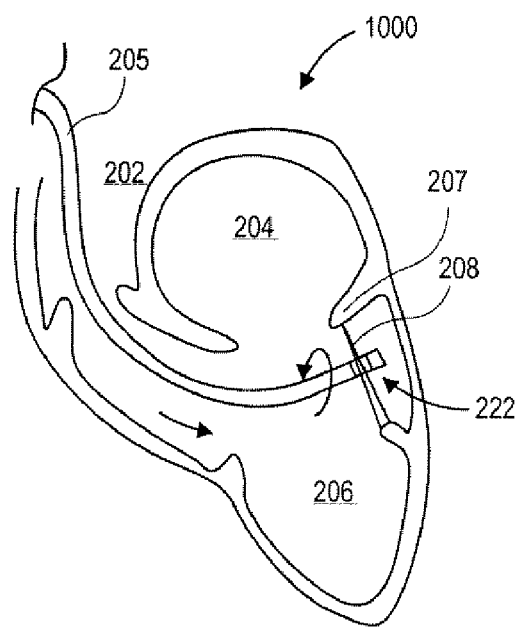
FIG. 10B

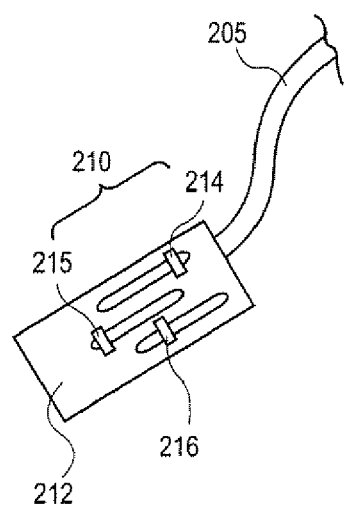
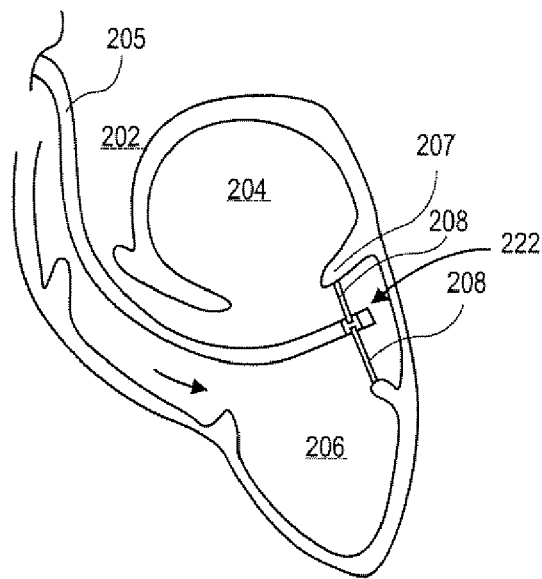
FIG. 10C
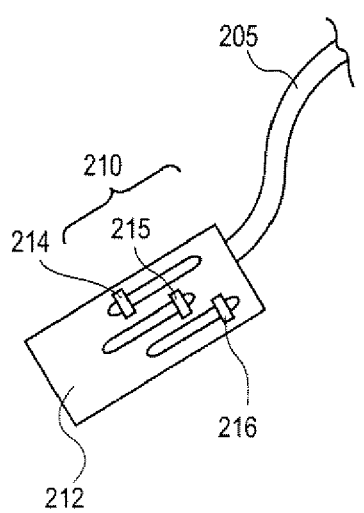
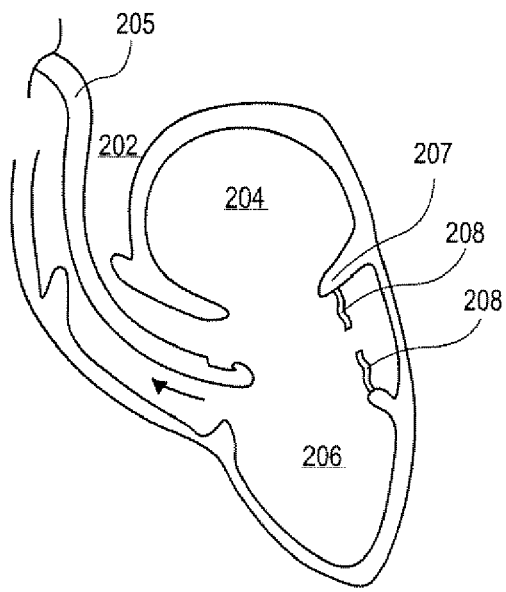
FIG. 10D

HEART VALVE CHORD CUTTER

TECHNICAL FIELD

The disclosure, in one embodiment, relates generally to the treatment of heart related diseases, and more particularly, in one embodiment, to the treatment of defective heart valves.

BACKGROUND

FIG. 1A illustrates a heart 10 with a partial internal view and arrows indicating the direction of blood flow within the heart. Four valves in the heart 10 direct the flow of blood within the left and right sides of the heart. The four valves include a mitral valve 20, an aortic valve 18, a tricuspid valve 60, and a pulmonary valve 62 as illustrated in FIG. 1A. The mitral valve 20 is located between the left atrium 12 and the left ventricle 14. The aortic valve 18 is located between the left ventricle 14 and the aorta 16. These two valves direct oxygenated blood coming from the lungs, through the left side of the heart, into the aorta 16 for distribution to the body. The tricuspid valve 60 is located between the right atrium 22 and the right ventricle 24. The pulmonary valve 62 is located between the right ventricle 24 and the pulmonary artery 26. These two valves direct de-oxygenated blood coming from the body, through the right side of the heart, into the pulmonary artery 26 for distribution to the lungs, where it again becomes re-oxygenated and distributed to the mitral valve 20 and the aortic valve 18.

The heart valves are complex structures. Each valve has "leaflets" that open and close to regulate the direction of blood flow. The mitral valve 20 has two leaflets and the tricuspid valve 60 has three leaflets. The aortic 18 and pulmonary 62 valves have leaflets that are referred to as "cusps," because of their half-moon like shapes. The aortic 18 and pulmonary 62 valves each have three cusps.

During diastole, the leaflets of the mitral valve 20 open, allowing blood to flow from the left atrium 12 to fill the left ventricle 14. During systole, the left ventricle 14 contracts, the mitral valve 20 closes (i.e., the leaflets of the mitral valve 20 re-approximate), and the aortic valve 18 opens allowing oxygenated blood to be pumped from the left ventricle 14 into the aorta 16. A properly functioning mitral valve 20 allows blood to flow into the left ventricle and prevents leakage or regurgitation of blood back into the left atrium (and subsequently back into the lungs). The aortic valve 18 allows blood to flow into the aorta 16 and prevents leakage (or regurgitation) of blood back into the left ventricle 14. The tricuspid valve 60 functions similarly to the mitral valve 20 to allow deoxygenated blood to flow into the right ventricle 24. The pulmonary valve 62 functions in the same manner as the aortic valve 18 in response to relaxation and contraction of the right ventricle 24 (i.e., to move de-oxygenated blood into the pulmonary artery 26 and subsequently to the lungs for re-oxygenation).

During relaxation and expansion of the ventricles 14, 24, (i.e., diastole), the mitral 20 and tricuspid 60 valves open, while the aortic 18 and pulmonary 62 valves close. When the ventricles 14, 24, contract (i.e., systole), the mitral 20 and tricuspid 60 valves close and the aortic 18 and pulmonary 62 valves open. In this manner, blood is propelled through both sides of the heart (as indicated by the arrows of FIG. 1A). The chordae tendineae are tendons linking the papillary muscles to the tricuspid valve in the right ventricle and the mitral valve in the left ventricle. As the papillary muscles contract and relax, the chordae tendineae transmit the resulting increase and decrease in tension to the respective valves, helping them to open and close properly. The chordae tendineae are string-like in appearance and are sometimes referred to as "heart strings." FIG. 1B illustrates an enlarged view of the mitral valve region of the heart with leaflets 25, 26 forming a coapted surface to prevent backflow of blood into the right atrium 12 from the left ventricle 14. Leaflet 26 is tethered by chordae 30, 31 to papillary muscle 27, and leaflet 25 is tethered by chordae 32, 33, and 34.

Regurgitation is a condition in which leaflets of a heart valve do not close completely, resulting in the backflow of blood. For instance, in a condition typically referred to as mitral valve regurgitation, the leaflets of the mitral valve do not close completely during systole and blood leaks back into the left atrium. Studies have shown that one effect of mitral valve regurgitation is the distortion or displacement of the left ventricle, as well as the papillary muscles to which the mitral valve leaflets are attached by the chordae. Displacement of the papillary muscles away from the mitral valve annulus tethers the leaflets into the left ventricle, thereby preventing the leaflets from closing effectively. FIG. 1C illustrates an enlarged view of the heart as shown by FIG. 1B, but with papillary muscle 27 displaced further down in left ventricle 14. Because of the displacement of papillary muscle 27, chordae 34 pulls on leaflet 25 eliminating the coapting surface between the leaflets. This allows oxygenated blood to flow back into the left atrium 12, and the heart is then forced to work harder to pump enough oxygenated blood to the body. This may lead to heart damage over a period of time. Regurgitation is common, occurring in approximately 7% of the population. Mitral valve regurgitation may be caused by a number of conditions, including genetic defects, infections, coronary artery disease (CAD), myocardial infarction (MI), or congestive heart failure (CHF).

Faulty or defective valves may be treated with various surgical procedures. Annuloplasty, for example, reduces the annular size of the mitral valve by placing a synthetic ring around the rim of the mitral valve. These types of procedures are typically major, invasive surgical procedures that may require opening the chest by sternotomy, making incisions in the chest wall, heart-lung bypass and suspending the beating of the heart. These invasive procedures subject patients to a tremendous amount of pain and discomfort and require lengthy recovery and/or hospitalization periods. Patients with congestive heart failure may not be able to tolerate the surgical procedures, leaving them with little or no alternative to treat their defective heart valves. Moreover, reducing the annular size alone may still leave the patient with regurgitation symptoms because the mitral valve leaflet may still be tethered by chordae to the displaced papillary muscles and ventricular walls.

SUMMARY OF THE DISCLOSURE

A medical device and method for percutaneously treating a heart valve is described. In one embodiment, the medical device includes a catheter having a proximal portion, a distal portion, and a notch formed near the distal portion. A cutting element may be disposed within the distal portion and is moveable across the notch to slice through a heart chord.

Additional embodiments, features and advantages of the medical device will be apparent from the accompanying drawings, and from the detailed description that follows below.

BRIEF DESCRIPTION OF THE DRAWINGS

The present disclosure is illustrated by way of example, and not limitation, in the figures of the accompanying drawings in which:

FIGS. 5A-5D illustrate alternative embodiments of steering tendons disposed within a catheter.

FIGS. 10A-10D illustrate one exemplary method for cutting a mitral valve chordae tendineae percutaneously.

DETAILED DESCRIPTION

Figure 1A:
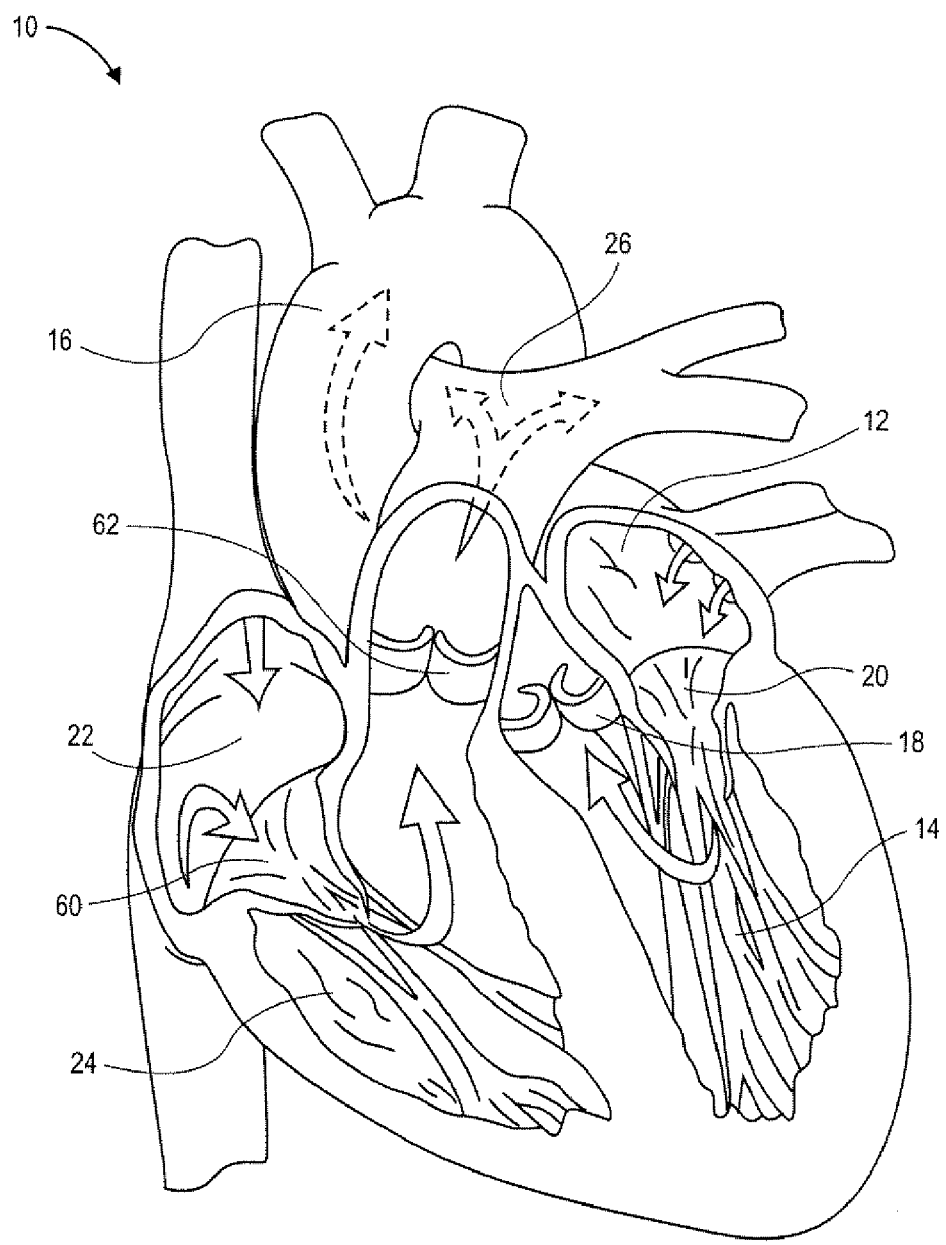
FIG. 1A illustrates a heart.
Figure 1B:
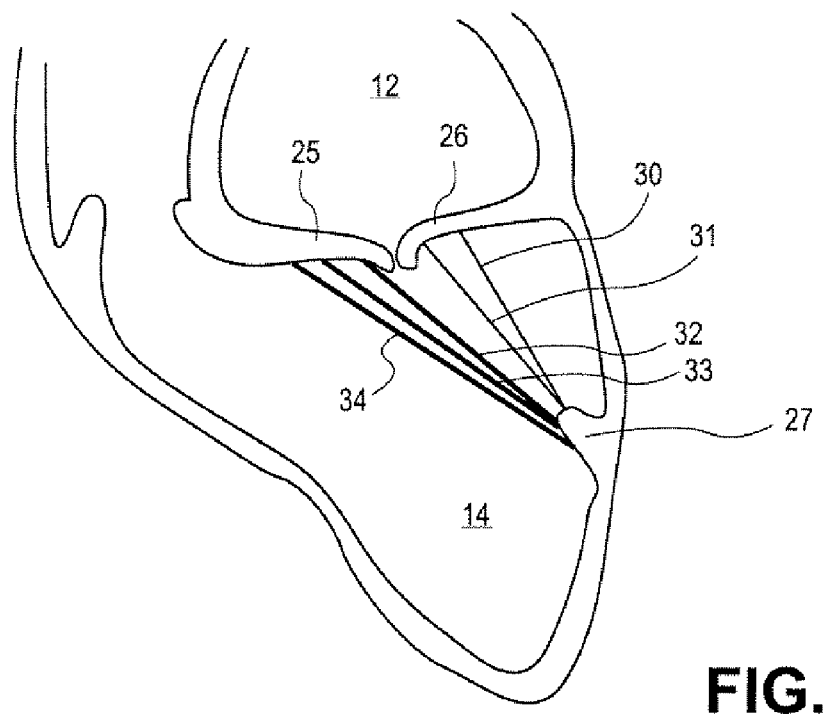
FIG. 1B illustrates an enlarged view of the mitral valve region of a heart.
Figure 1C:
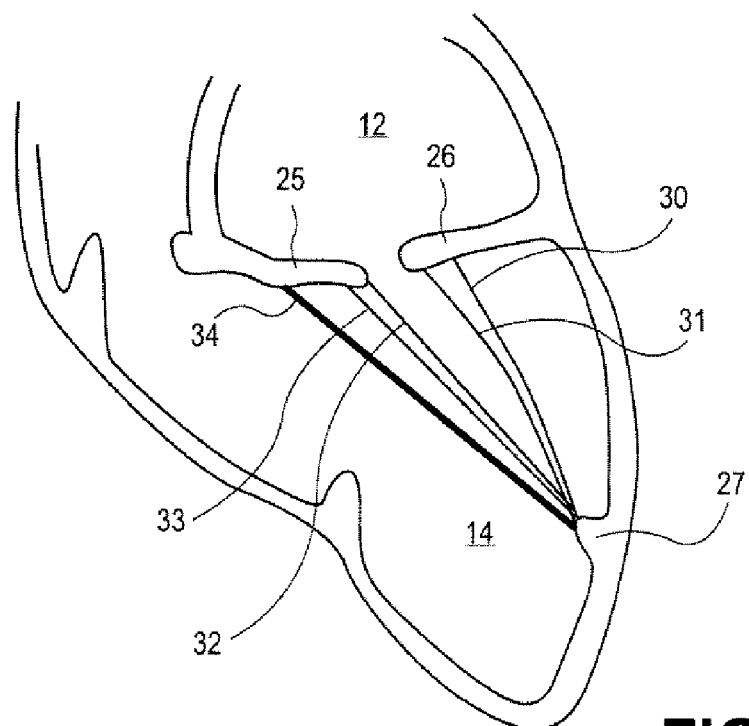
FIG. 1C illustrates another enlarged view of the mitral valve region of the heart.

In the following description, numerous specific details are set forth such as examples of specific materials or components in order to provide a thorough understanding of the present disclosure. It will be apparent, however, to one skilled in the art that these specific details need not be employed to practice the disclosure. In other instances, well known components or methods have not been described in detail in order to avoid unnecessarily obscuring the present disclosure. Embodiments of a medical device discussed below are described with respect to the treatment of a mitral valve. It may be appreciated, however, that other heart valves or body tissue may be treated, and embodiments of the medical device are not limited in their applicability to treating the mitral valve.

Embodiments of a medical device and methods for treating the mitral valve percutaneously are described. A medical device, in one embodiment, may be used to treat mitral valve regurgitation or prolapse by severing a mitral valve chordae tendineae that prevents the proper closing of a mitral valve leaflet during systole. In one embodiment, the medical device includes an elongated catheter having a proximal portion and a distal portion. The distal portion may have a notch or an aperture window appropriately sized for positioning a cardiac tissue or heart valve chord (e.g., a chordae tendineae tethered to a mitral valve leaflet) therein. A cutting element may be disposed within a lumen formed within the elongated catheter and positioned near the distal portion. The cutting element may be moved or actuated across the notch to slice through the cardiac tissue (e.g., one or more selected chordae) positioned within the notch. In one embodiment, the cutting element may be a sharp blade. In another embodiment, the blade may be coupled to a control mechanism disposed near a proximal portion of the catheter and outside of a patient. The control mechanism may be handled by an operator to move the blade back and forth across the notch. In one embodiment, the blade may slice through a cardiac tissue by a retracting action that moves the blade from a first position distal to the notch to a second position proximal to the notch. In an alternative embodiment, a cutting element may be disposed internally in a catheter and be moved through a slot in the catheter wall to a position outside of the catheter, thereby allowing the cutting element to cut one or more selected chordae. In this alternative embodiment, the catheter does not include a notch.

In one method for treating mitral valve prolapse caused by an elongated chordae tendineae, the chordae may be severed with a medical device that is percutaneously advanced to the target chordae. The medical device may include an elongated catheter having a proximal portion and a distal portion, with a notch formed near the distal portion for securing the medical device to the chordae. A cutting element may be disposed within the catheter near the distal portion, and moveable across the notch to slice through the chordae. In one embodiment, the distal portion of the elongated catheter may be inserted into a patient through, for example, the femoral artery, down the aortic valve, and into the left ventricle. The medical device may also include a control mechanism disposed near the proximal portion of the catheter that has one or more handles for steering the distal portion of the catheter for advancement into the left ventricle. In one embodiment, one or more steering tendons may extend from the control mechanism to the distal portion of the catheter to provide steerability to the catheter. The control mechanism may also include a separate handle coupled to a wire that extends from the handle and coupled to the cutting element. The handle may by used to cause a forward or reverse movement of the cutting element across the notch to slice through the chordae. In one embodiment, the cutting element, which may be a blade, may be retracted from a first position distal to the notch to a second position proximal to the notch using a handle disposed on a control mechanism. This exemplary embodiment provides an advantage of percutaneously treating mitral valve prolapse without the need for invasive surgical procedures.

Figure 11A:
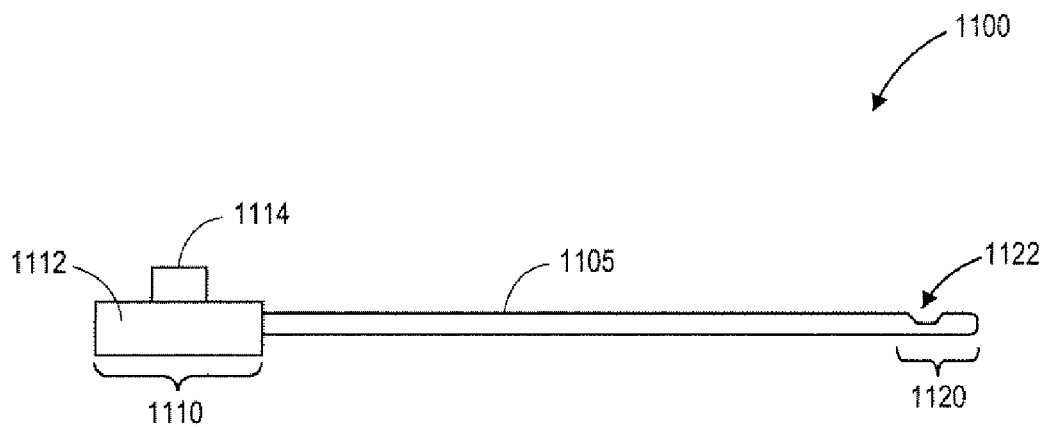
FIGS. 11A-11B illustrate one embodiment of a medical device to treat a heart valve.
Figure 11B:
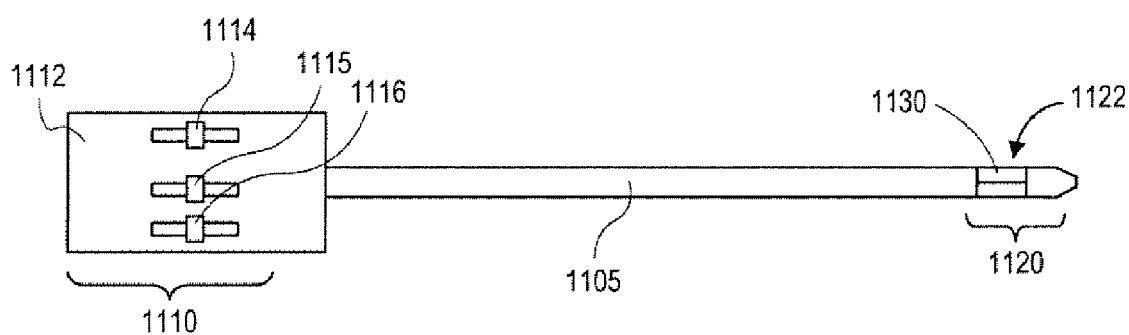

Referring now to FIGS. 11A-11B, side and top views of one embodiment of a medical device to treat a heart valve are illustrated. Medical device 1100, in one embodiment, may be used to cut one or more heart chords (e.g., a mitral valve chordae) percutaneously. FIG. 11A shows a side view of medical device 1100 having a proximal portion 1110, an elongated catheter portion 1105, and a distal portion 1120. Elongated catheter portion 1105 is not drawn to scale and may be of an appropriate length to reach a target region within a patient. Elongated catheter may be substantially tubular and may be appropriately sized to fit within lumens of a patient (e.g., arteries and vessels). Proximal portion 1110 includes a control mechanism 1112 having one or more handles or control elements (e.g., handle 1114). Distal portion 1120 includes a notch 1122 formed into the catheter body. A top view of medical device 1100, as illustrated by FIG. 11B, shows notch 1122 having a width substantially similar to a diameter of catheter 1105. The opening formed by notch 1122 also shows a wire 1130 disposed within catheter 1105. As described in greater detail below, wire 1130, in one embodiment, may be coupled at one end to a cutting element (not shown) disposed near the distal portion 1120, and to a handle (e.g., handle 1115) at the opposite end. When a heart chord (e.g., mitral valve chordae) is positioned across notch 1122, a cutting element (e.g., a blade) may be moved from one side of the notch to the opposite side of the notch, in a direction of the elongated catheter, to slice through or cut the chord. Control mechanism 1112 disposed near proximal portion 1110 may have one or more handles (e.g., handles 1114, 1115, 1116) to provide operability to medical device 1100, including steerability of distal portion 1120 and the actuation of the cutting element back and forth across notch 1122.

Figure 2:
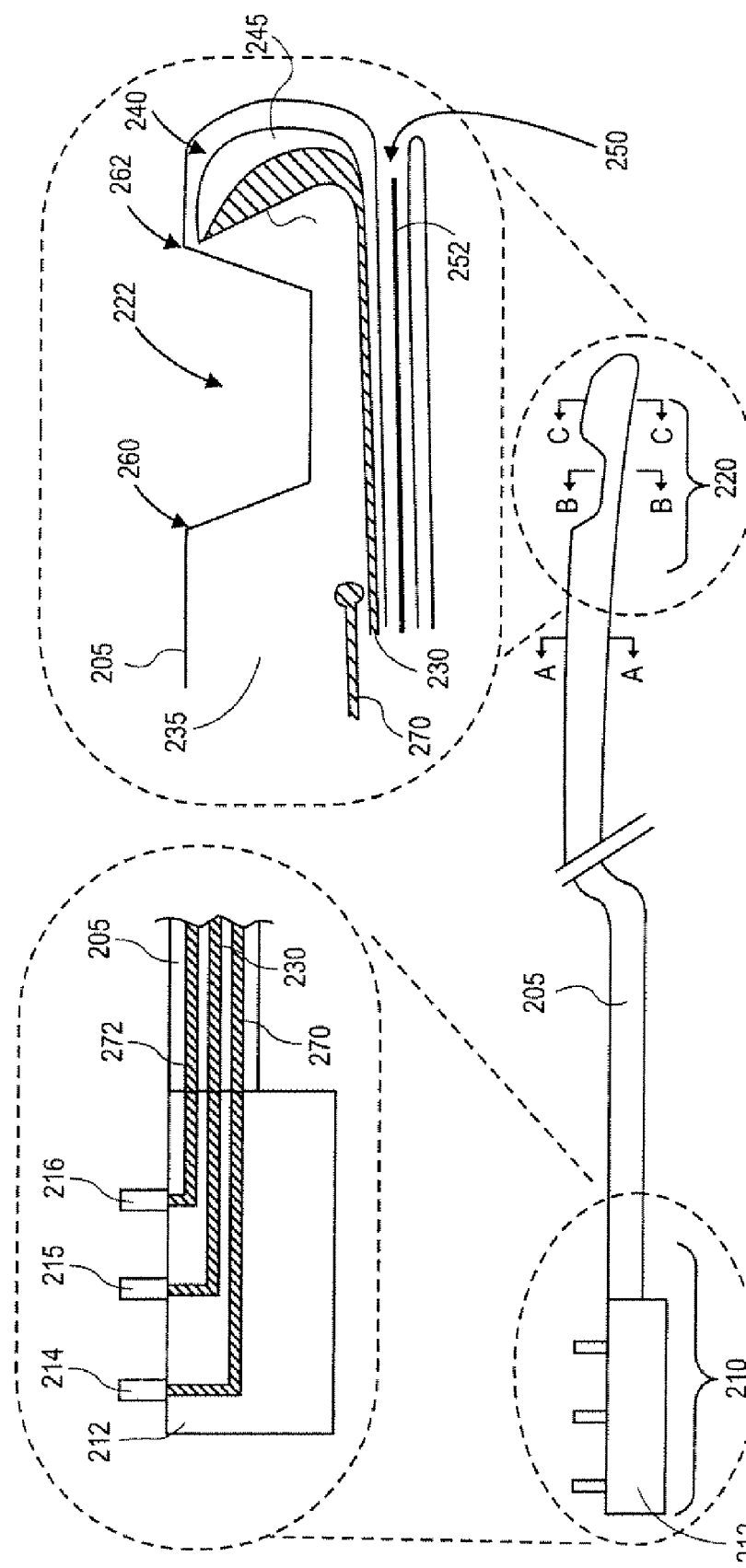
FIG. 2 illustrates a side view of a medical device that may be used to cut a heart chord percutaneously.

FIG. 2 illustrates another side view of a medical device 200 that may be used to cut a heart chord percutaneously. An enlarged view of distal portion 220 shows notch 222 formed within catheter 205. Notch 222 has a first proximal side 260 and a second distal side 262 along a longitudinal length of catheter 205. A lumen 235 is also formed within catheter 205 extending down to the distal portion 220. A cutting element 240 may be disposed within lumen 235. In one embodiment, cutting element 240 may include a blade portion 242 that may be partially covered by blade support 245. Blade support 245 may provide rigidity and mechanical support to blade portion 242 when slicing through a heart chord and may also protect heart tissue from the back side of the blade. In may be appreciated by one of skill in the art that cutting element 240 may only include blade portion 242, without blade support 245. In one embodiment, cutting element 240 may be made of a uniform material, including various types of metal that may be contemplated for a blade (e.g., stainless steel). Alternatively, blade support 245 and blade portion 242 may be made of different materials. For example, blade portion 242 may be made of stainless steel, and blade support may be made of a polymer.

In one embodiment, cutting element 240 may be positioned near the distal side 262 of notch 222 (as shown in FIG. 2) such that no portion of cutting element (e.g., blade portion 242 or blade support 245) extends out into notch 222. Blade support 245 may be coupled to a wire 230 that extends to proximal portion 210 and that is coupled to control mechanism 212. Distal portion 220 also shows a steering tendon 270 extending to a point near proximal side of notch 222. Steering tendon 270 may be coupled to an inner surface of catheter 205 within lumen 235. Steering tendon 270 enables distal portion 220 to be steered and flexed to a desired orientation. In one embodiment, steering tendon 270 may be controlled by a handle disposed on a control mechanism (e.g., control mechanism 212). Distal portion 220 may have multiple steering tendons disposed therein. Steering tendons are well known in the art; accordingly, a detailed description is not provided. An optional guidewire lumen 250 may also be formed within catheter 205 which may be used to advance a guidewire 252 therethrough. As described in greater detail below, guidewire 252 may be used to percutaneously advance distal portion 220 of device 200 to a region in the patient's heart.

An enlarged view of proximal portion 210 shows catheter 205 coupled to control mechanism 212. Control mechanism includes handles 214, 215, 216. In one embodiment, handle 214 may be coupled to steering tendon 270, handle 216 may be coupled to a second steering tendon 272, and handle 215 may be coupled to wire 230. Handles 214, 215, 216 may be moved forwards and backwards within slots formed on control mechanism 212. For example, handle 215 may be moved forwards and backwards to move cutting element 240 across notch 222. In an alternative embodiment, handles 214, 216 that control steering tendons 270, 272, respectively may be knobs that rotate to produce a steering effect of tendons 270, 272.

Figure 2C:
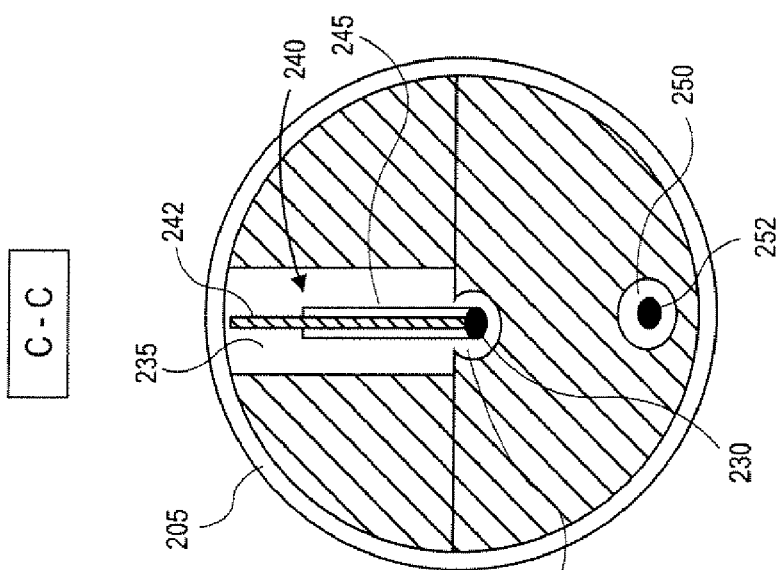
FIG. 2C illustrates a cross-sectional view of the device illustrated in FIG. 2.
Figure 2B:
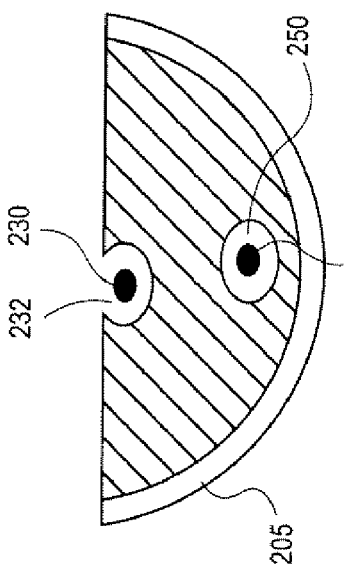
FIG. 2B illustrates a cross-sectional view of the device illustrated in FIG. 2.
Figure 2A:
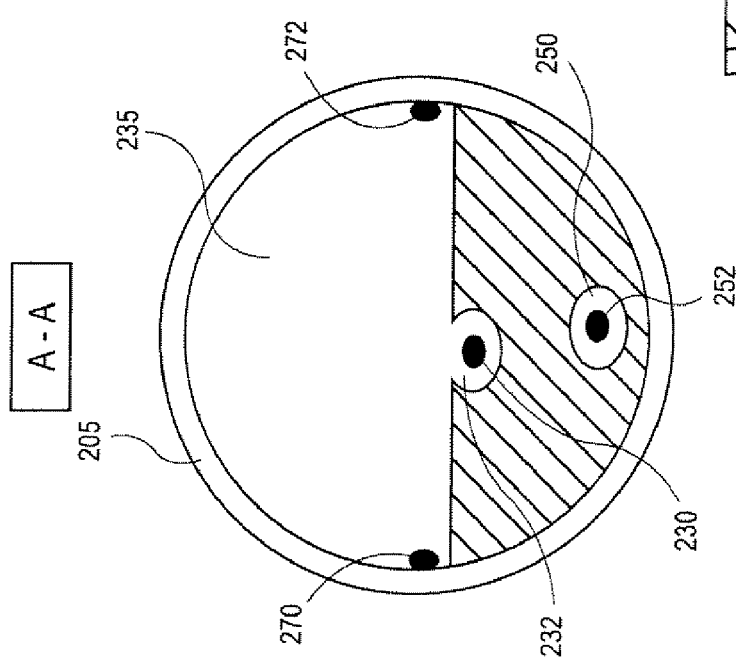
FIG. 2A illustrates a cross-sectional view of the device illustrated in FIG. 2.

FIG. 2A illustrates a cross-sectional view of device 200 taken along line A-A near distal portion 220. This view of device 200 near proximal side 260 of notch 222 has lumen 235 formed within catheter 205. Lumen 235 has a hemispherical shape with steering tendons 270, 272 attached to an inner surface of catheter 205 within lumen 235. Wire 230 sits in a groove 232 formed within lumen 235. Groove 232 may be sized to secure wire 230 therein, and to prevent wire 230 from freeing itself and releasing into lumen 235. Catheter 205 also has a guidewire lumen 250 for advancing a guidewire 252 therein. FIG. 2B illustrates a cross-sectional view of device 200 taken along line B-B of FIG. 2A between a proximal side 260 and a distal side 262 of notch 222. This part of device 200 does not have lumen 235 formed by catheter 205. Groove 232 which secures wire 230, as well as guidewire lumen 250 having guidewire 252 disposed therein, extend through this part of device 200. FIG. 2C illustrates a cross-sectional view of device 200 taken along line C-C of FIG. 2A near distal side 262 of notch 222. Catheter 205 forms lumen 235 with cutting element 240 positioned therein. In one embodiment, lumen 235 distal to notch 222 may be narrowed to form slightly wider than groove 232. The shape and size of lumen 235 distal to notch 222 prevent cutting element 240 from tilting when positioned within the distal portion 220 of catheter 205. Alternatively, lumen 235 near distal to notch 222 may be formed substantially similar to the view shown in FIG. 2C. Blade support 245 partially covers blade portion 242 of cutting element 240, with blade support 245 sitting in groove 232. The nearly closed shape of groove 232 enables cutting element to remain upright. As described in greater detail below, groove 232 may have alternative designs to support cutting element 240. Guidewire lumen 250 having guidewire 252 also extends through this part of device 200.

Figure 3A:
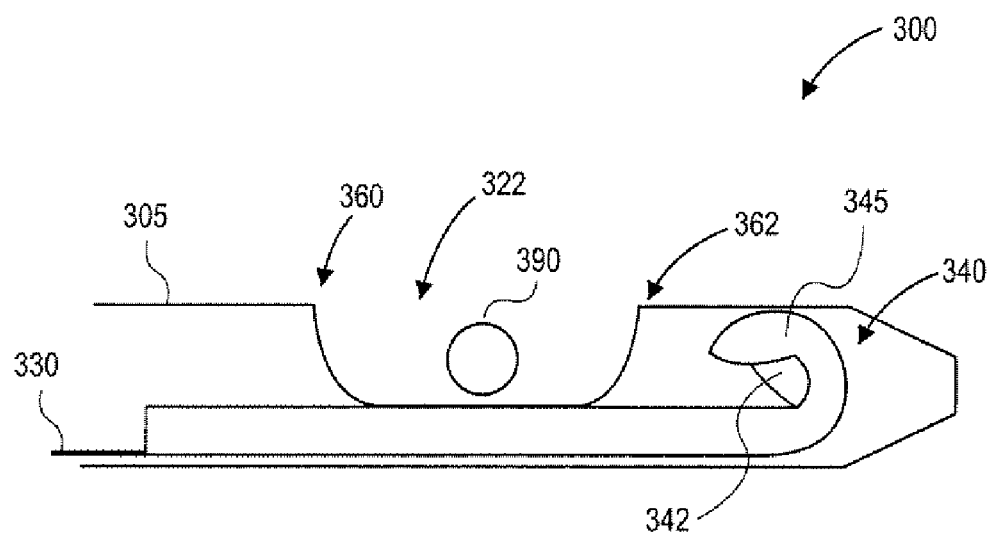
FIGS. 3A-3D illustrate one exemplary embodiment of the mechanical action of a cutting element disposed within a medical device.
Figure 3B:
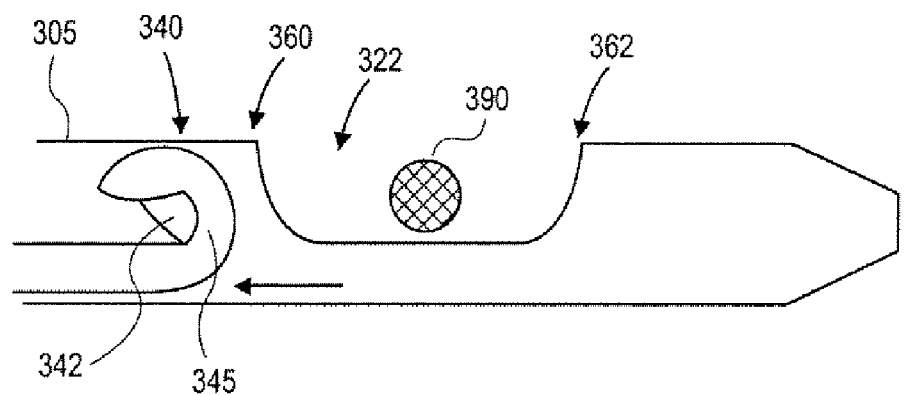

FIGS. 3A-3D illustrate one exemplary embodiment of the mechanical action of a cutting element disposed within a medical device (e.g., device 200 described above). FIG. 3A illustrates a side view of a distal portion 300 of catheter 305 with a heart chord 390 (e.g., a mitral valve chordae) positioned within a notch 322 formed within catheter 305. Notch 322 has a first proximal side 360 and a second distal side 362 with chord 390 positioned between them. Cutting element 340 is disposed within catheter 305 and positioned near distal side 362 of notch 322. Cutting element 340 includes a blade portion 342 partially covered by blade support 345. In one embodiment, blade portion 342 may be slightly curved, although as described in greater detail below, alternative designs for blade portion 342 may be used. Blade support 345 may extend from the distal side 362 to the proximal side 360 of notch 322, and coupled to wire 330. In an alternative embodiment, blade support 345 may be relatively short, and not extend a length from a distal side 362 to a proximal side 360 of notch 322. By pulling on wire 330 (e.g., with a handle on a control mechanism 212), cutting element 340 may be retracted from a position near distal side 362 of notch 322 to the proximal side 360. In doing so, blade portion 342 slices through chord 390, as illustrated by FIG. 3B. Cutting element 340 may then be returned near distal side 362 of notch 322 to perform another cutting procedure (e.g., to cut another chord).

Figure 3C:
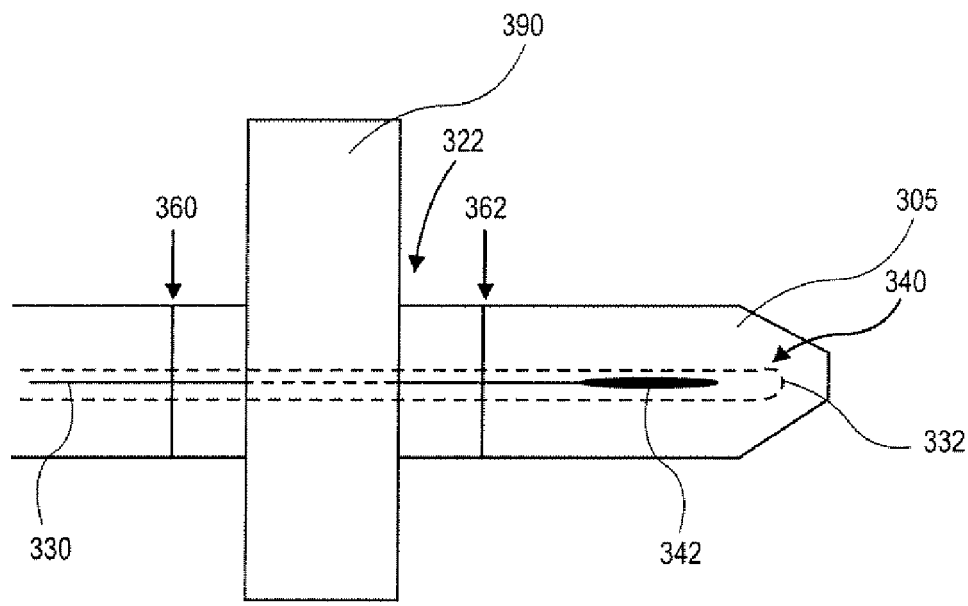
Figure 3D:
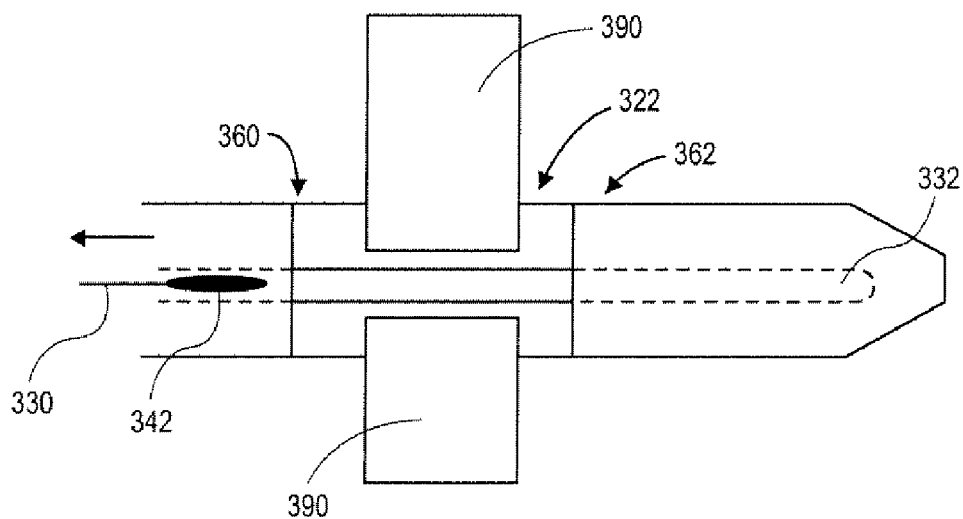

FIG. 3C illustrates a top view of distal portion 300 of catheter 305. The view shown may be that of cutting element 340 positioned near a distal side 362 of notch 322 illustrated in FIG. 3A. A groove 332 extends within catheter 305 of distal portion 300. In one embodiment, groove 332 serves as track for cutting element 340 to move longitudinally within catheter 305. As discussed above, groove 332 may be shaped to secure blade support 345 and wire 330. As shown in FIG. 3D, cutting element 340, with blade portion 342, is retracted linearly within catheter 305 along groove 332 to slice through chord 390.

Figure 4A:
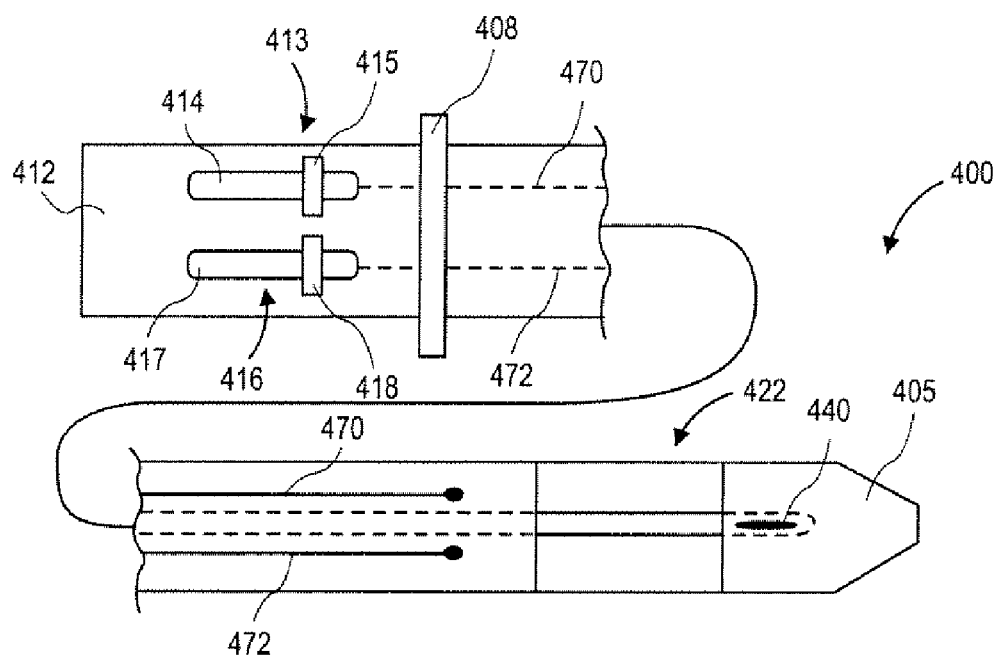
FIGS. 4A-4B illustrate one embodiment of steering tendons disposed within a catheter to provide steering capabilities.
Figure 4B:
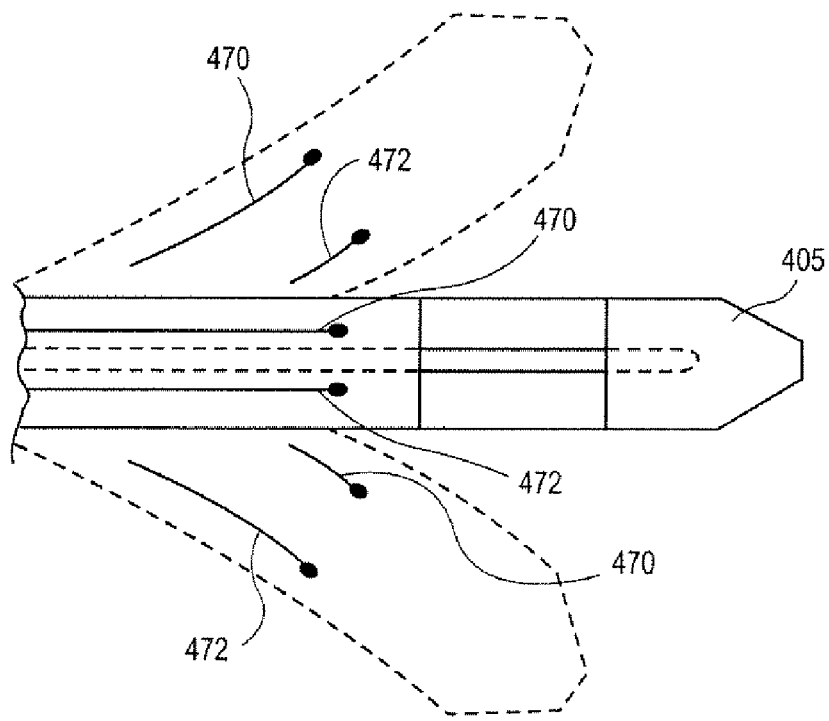

As described above, embodiments of a medical device described herein may have steering capabilities to advance a cutting element disposed within a distal portion of a catheter to a target region in a patient's heart. FIGS. 4A-4B illustrate one embodiment of steering tendons disposed within the catheter to provide steering capabilities. FIG. 4A shows a top view of a distal portion 400 of catheter 405. Tendons 470, 472 extend within an inner surface of catheter 405 from a point proximal to notch 422 back to control mechanism 412 that may be disposed near a proximal portion of catheter 405. A cutting element 440 is positioned distal to notch 422 and may be moved in the manner described above, relative to notch 422 to cut a chord. Tendon 470 may be coupled to handle 413 and tendon 472 may be coupled to handle 416. Handle 413 may include lever 415 slidable along slot 414, and handle 416 may include lever 418 slidable along slot 417. In one embodiment, sliding lever 415 along slot 414 may pull tendon 470 to steer distal portion 400 of catheter 405 in a particular direction. Analogously, sliding lever 418 along slot 417 may pull tendon 472 to steer distal portion 400 of catheter 405 in a direction opposite to that steered by tendon 470. FIG. 4B shows one embodiment of a range of motion of distal portion 400 that may achieved by pulling on tendons 470, 472 with handles 413, 416 disposed on control mechanism 412. Control mechanism 408 may also include a knob 408 that enables catheter 405 to be rotated about a longitudinal axis. The ability to rotate distal portion 400, along with the steering abilities provided by steering tendons 470, 472 enables an operator to position a heart chord within notch 422.

FIGS. 5A-5D illustrate alternative embodiments of steering tendons disposed within a catheter 405. As illustrated by these cross-sectional views, the number of tendons and the position of the tendons within catheter 405 may be variable, and not limited to the two tendons (470, 472) described above. Tendons (e.g., tendons 470, 472, 474, 476) may be disposed in different orientations with respect to groove 432 formed within catheter 405. For example, the use of four tendons as shown by FIG. 5D may provide the maximum amount of steerability to catheter 405. In one embodiment, each tendon shown in FIG. 5D may be coupled to individual control handles on control mechanism 412.

Figure 6C:
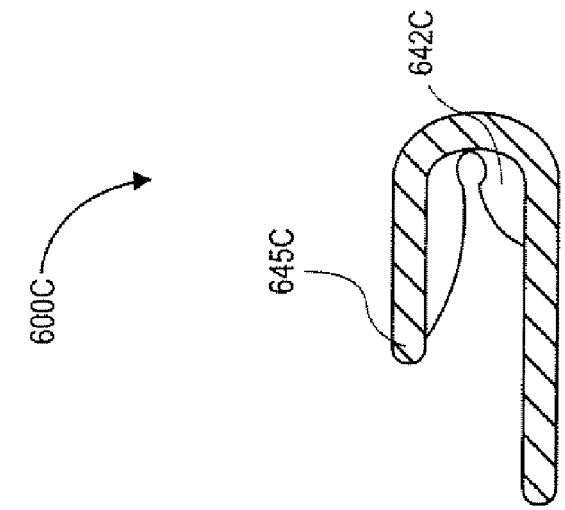
FIGS. 6A-6C illustrate side views of alternative embodiments for a cutting element that may be disposed within a medical device.
Figure 6B:
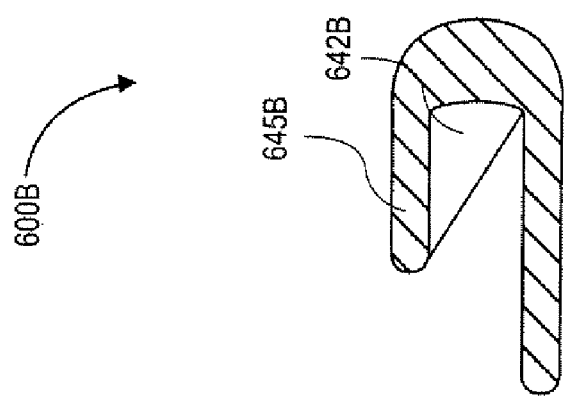
Figure 6A:
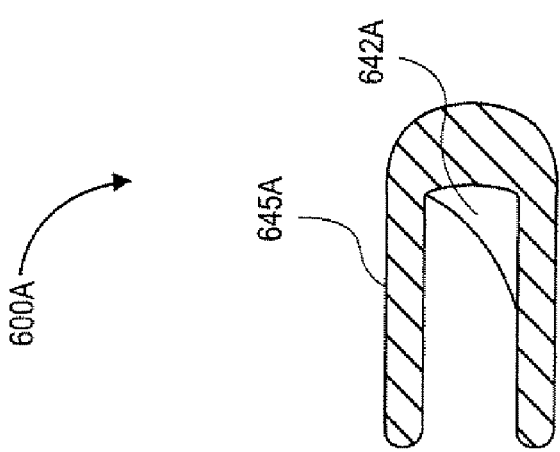

FIGS. 6A-6C illustrate side views of alternative embodiments for a cutting element that may be disposed within embodiments of a medical device described herein (e.g., cutting element 340 described with respect to FIG. 3 or cutting element 240 of FIG. 2). For example, FIG. 6A illustrates cutting element 600A with blade support 645A forming a slot with a cutting edge of blade portion 642A extending from a top portion of the slot to a bottom portion of the slot, but substantially disposed within the slot. FIG. 6B illustrates cutting element 600B with blade support 645B forming a smaller slot compared to the slot formed by the embodiment of FIG. 6A. Cutting edge of blade portion 642B extends from an outer end of a top portion of blade support 645B to an inner end of bottom portion of blade support 645B. FIG. 6C illustrates yet another embodiment of cutting element 600C with blade support 645C forming a slot analogous to that formed by blade support 645B of FIG. 6B. Blade portion 642C forms two cutting edges extending along a top portion and a bottom portion of blade support 645C.

Figure 7C:
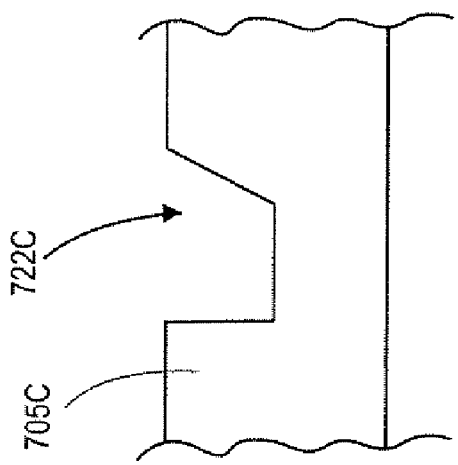
FIGS. 7A-7C illustrate side views of alternative embodiments for notch designs that may be formed within a distal portion of a medical device.
Figure 7B:
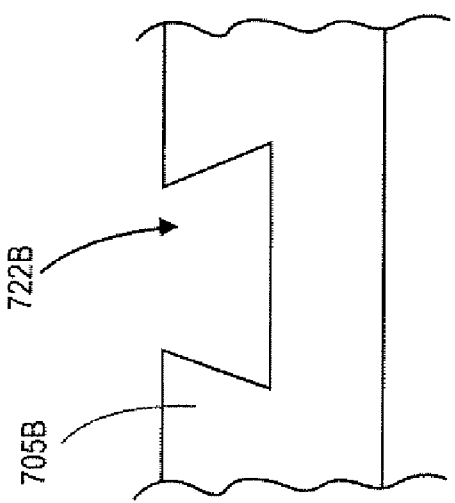
Figure 7A:
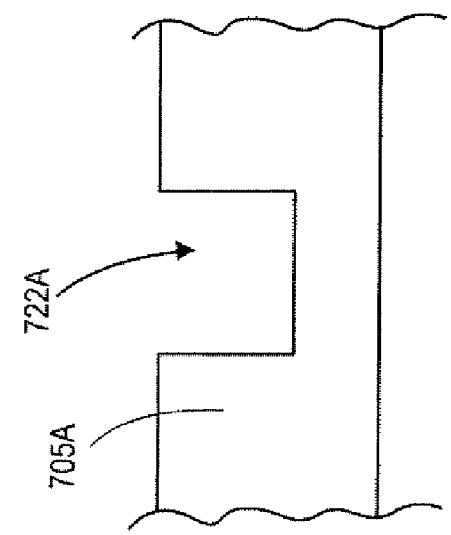

FIGS. 7A-7C illustrate side views of alternative embodiments for notch designs that may be formed within a distal portion of a medical device to cut heart chords (e.g., notch 322 described with respect to FIG. 3). For example, FIG. 7A shows a notch 722A having a substantially square design formed within catheter 705A. FIG. 7B shows a notch 722B that opens to a larger size within catheter 705B. FIG. 7C shows yet another embodiment of notch 722C formed within catheter 705C in which one side of notch 722C may be slightly curved and an opposite side may be substantially straight. In one embodiment, the notches described herein may have a depth of about 0.5 mm to 1.5 mm and a length of about 1 mm to 4 mm.

Figure 8A:
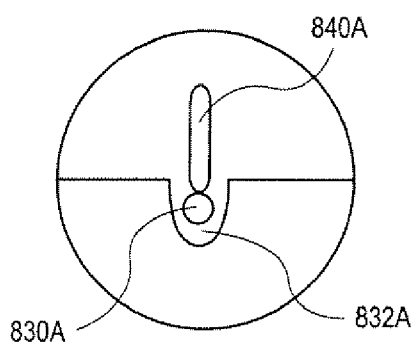
FIGS. 8A-8D illustrate cross sectional views of alternative embodiments for a groove that may be formed within a medical device.
Figure 8B:
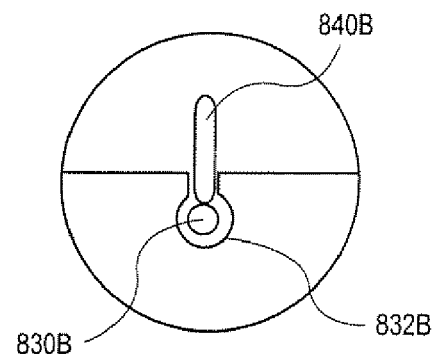
Figure 8C:
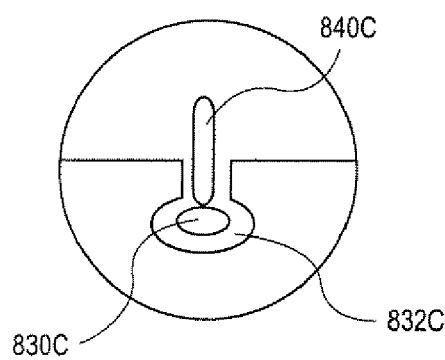
Figure 8D:
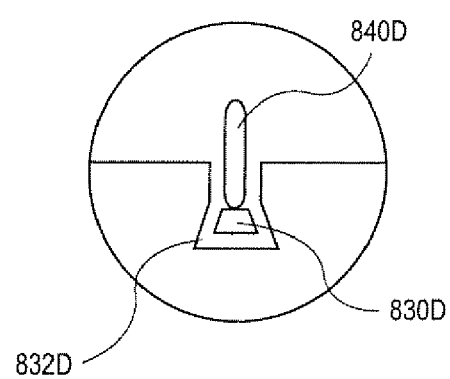

FIGS. 8A-8D illustrate cross sectional views of alternative embodiments for a groove that may be formed within embodiments of a medical device described herein (e.g., groove 232 described with respect to FIG. 2 and cross sectional view FIG. 2C). In one embodiment, the groove formed within a catheter provides support to keep the cutting element upright and prevent tilting while the cutting element moves within the catheter. The shape of the groove may also serve to prevent the wire and/or cutting element from popping out during movement. The groove also provides a track so that the cutting element may maintain a linear path when pulled by the wire disposed within the groove. In one embodiment, a cross-sectional design of the wire may determine the corresponding design of the groove. For example, FIG. 8A shows wire 830A having a substantially spherical design and groove 832A having a hemispherical design to accommodate the design of wire 830A. Cutting element 840A is shown coupled to wire 830A. FIG. 8B shows another embodiment of a groove design for a substantially spherical wire 830B in which groove 832B has a substantially straight portion that opens up to substantially spherical groove. A portion of cutting element 840B may sit deeper in groove 832B compared to cutting element 840A. FIG. 8C shows another embodiment of a groove design in which wire 830C has a substantially elliptical shape with groove 832C also having a substantially elliptical shape. FIG. 8D shows yet another embodiment of a groove design in which wire 830D may have a substantially trapezoidal shape with groove 832D having a similar design to accommodate wire 830D. The embodiments for a groove shown in FIGS. 8B-8D may be especially effective in preventing a wire from popping of the groove during movement of the cutting element. Moreover, because a portion of cutting element is embedded within the grooves in these embodiments, rotation of the cutting element may be effectively prevented.

Figure 9A:
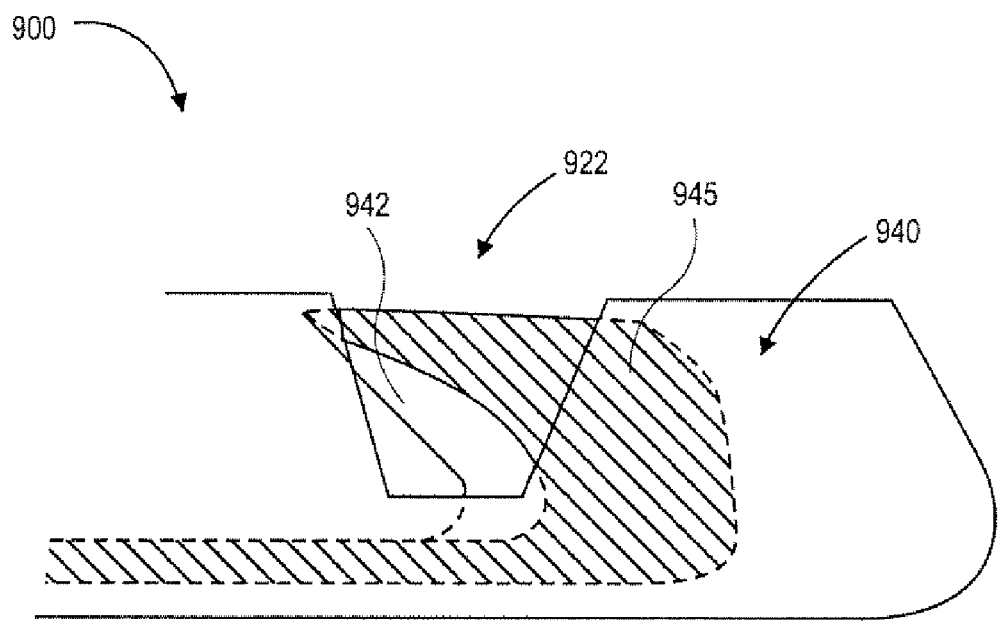
FIGS. 9A-9B illustrate an alternative embodiment for preventing rotation of a cutting element disposed within a catheter.
Figure 9B:
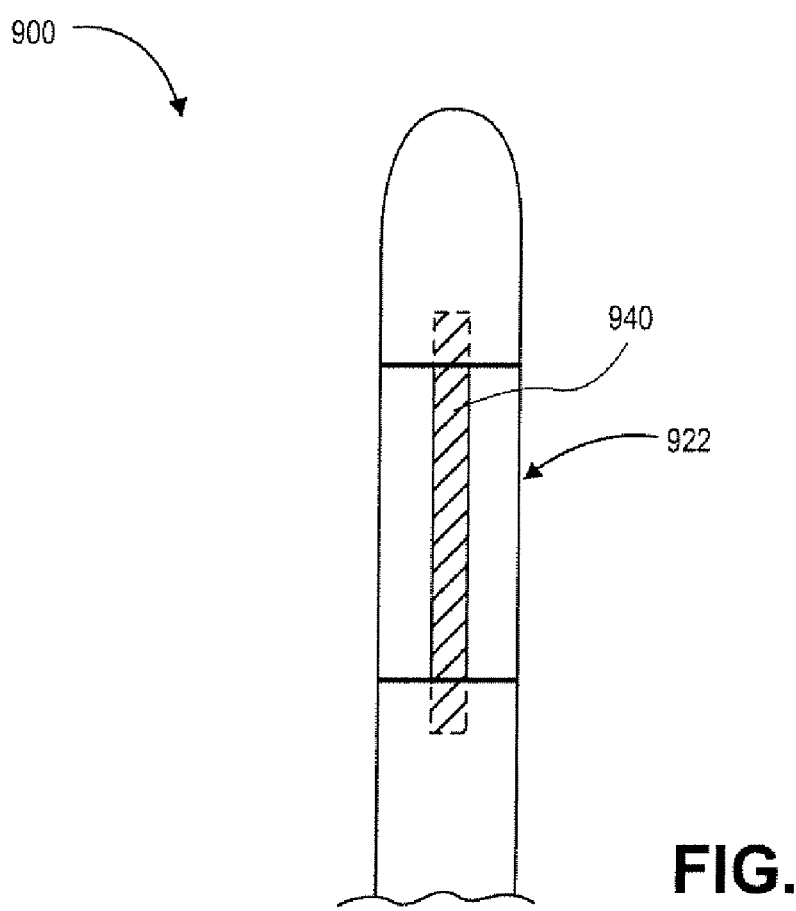

FIGS. 9A-9B illustrate an alternative embodiment for preventing rotation of a cutting element disposed within a catheter. In this embodiment, a longitudinal length of the notch is made shorter than the cutting element such that a portion of the cutting element is always contained within the catheter. Additionally, a width of the catheter may be just large enough to contain the cutting element and prevent its rotation. FIG. 9A shows a side view of catheter 900 having a cutting element 940 overlapping a size of notch 922. FIG.

9B shows a top view of catheter 900 with cutting element 940 spanning across a longitudinal length of notch 922. Because cutting element 940 is longer than notch 922, the cutting element 940 tends not to rotate when exposed in notch 922.

FIGS. 10A-10D illustrate one exemplary method for cutting a mitral valve chordae tendineae percutaneously. In one embodiment, the medical device used to cut the chordae may be device 200 described above with respect to FIG. 2. FIG. 10A illustrates a simplified, cross-sectional view of a left side of a heart including aortic arch 202, left atrium 204 and left ventricle 206. A chordae tendineae 208 attaches a mitral valve leaflet 207 with a tissue portion of left ventricle 206. For the purposes of describing a method to cut a target chordae, only chordae 208 is shown, although it may be understood that more than one chordae may be cut with device 200. A distal portion of catheter 205 has been percutaneously advanced into the left ventricle 206. In one embodiment, a guidewire (not shown) may be initially advanced into the left ventricle by inserting the guidewire into, for example, the femoral artery, down the aortic arch 202, and into left ventricle 206. Catheter 205 may be loaded and tracked over the guidewire to be positioned near chordae 208 (e.g., through guidewire lumen 250 formed within catheter 205). In alternative embodiments, catheter 205 may be any of the catheter types used in the art, including but not limited to "rapid exchange" (RX) catheters, "over-the-wire" (OTW) catheters, or a "tip RX" catheters. If a guidewire is utilized, the guidewire may be removed after the distal portion of catheter 205 has entered the left ventricle. Various imaging techniques known in the art may also be used to locate chordae 208. For example, echo imaging, infrared illumination, x-ray, and magnetic resonance imaging methods may be utilized. These imaging techniques are known in the art; accordingly, a detailed description is not provided.

Catheter 205 extends back to a proximal portion 210 disposed outside of a patient. Catheter 205 may be coupled to a control mechanism 212 which includes control handles 214, 215, 216. The control handles may be used, in one embodiment, to steer and/or rotate the distal portion of catheter 205, in particular, to position notch 222 around chordae 208. For example, handles 214, 216 may be manipulated to steer and/or rotate catheter 205 (e.g., with steering tendons 270, 272 described above) to position chordae 208 within notch 222 as illustrated by FIG. 10B. With notch 222 positioned around chordae 208, handle 215 disposed on control mechanism may be pulled (in the direction of the arrow as indicated in FIG. 10C) to retract a cutting element (e.g., cutting element 240) disposed within catheter 205 from a position on a distal side to a proximal side of notch 222. In one embodiment, the action of the cutting element may be that described above with respect to cutting element 340 of FIGS. 3A-3B. FIG. 10D shows chordae 208 having been cut into two portions. Catheter 205 may then be tracked back up the aortic arch 202 and out of the patient or alternatively, notch 222 may be positioned over another target chordae to be severed. For example, handles 214, 216 may be used to steer catheter 205 to another target chordae, and handle 215 used to reposition the cutting element near a distal side of notch 222.

In one embodiment, a heart chord cutting method discussed herein may be combined with another approach for treating a defective mitral valve (e.g., mitral valve regurgitation). This additional approach includes applying a support member in the coronary sinus near the mitral valve region or applying a support member on the mitral valve itself, such as on the mitral valve annulus, or applying a first support member in the coronary sinus and applying a second support member on the mitral valve annulus. In this embodiment, a general technique would include cutting percutaneously one or more heart chords and also applying percutaneously a support member on the mitral valve or applying a support member in the coronary sinus. The combination of percutaneous chord cutting with this additional percutaneous approach should provide improved mitral valve functionality. These additional approaches are described in several co-pending U.S. patent applications which are hereby incorporated by reference, these applications being: (1) Apparatus and Methods for Heart Valve Repair, by inventors Gregory M. Hyde, Mark Juravic, Stephanie A Szobota, and Brad D. Bisson, filed Nov. 15, 2002, Ser. No. 10/298,133; (2) Heart Valve Catheter, by inventor Gregory M. Hyde, filed Nov. 15, 2002, Ser. No. 10/295,071; (3) Valve Adaptation Assist Device, by inventors William E. Webler, James D. Breeding, Brad D. Bisson, Firas Mourtada, Gregory M. Hyde, Stephanie A. Szobota, Gabriel Asongwe, and Jeffrey T. Ellis, filed Nov. 15, 2002, Ser. No. 10/712,553; (4) Valve Annulus Constriction Apparatus and Method, by inventors Peter L. Callas and Richard Saunders, filed Nov. 15, 2002, Ser. No. 10/295,323; (5) Methods for Heart Valve Repair, by inventors William E. Webler, Gregory M. Hyde, Christopher Feezor and Daniel L. Cox, filed Nov. 15, 2002, Ser. No. 10/295,714; and (6) Apparatus and Methods for Heart Valve Repair, filed Oct. 15, 2002, Ser. No. 11/240,589.

A kit (e.g., a kit of multiple catheters with instructions) maybe used to perform the combination of the percutaneous chord cutting with another percutaneous approach (e.g., such as applying percutaneously a mitral valve annulus). For example, a first catheter, such as catheter 205 described above, may be combined with a kit with a second catheter designed to apply a member percutaneously, such as a support annulus to the mitral valve region or a stent-like structure in the coronary sinus near the mitral valve. The second catheter may be used to deploy a support annulus around the mitral valve annulus to reshape the mitral valve, or a set of joined clips which grasp mitral valve leaflets, or a stent or ring or stent-like structure in the coronary sinus to reshape the mitral valve.

Figure 12A:
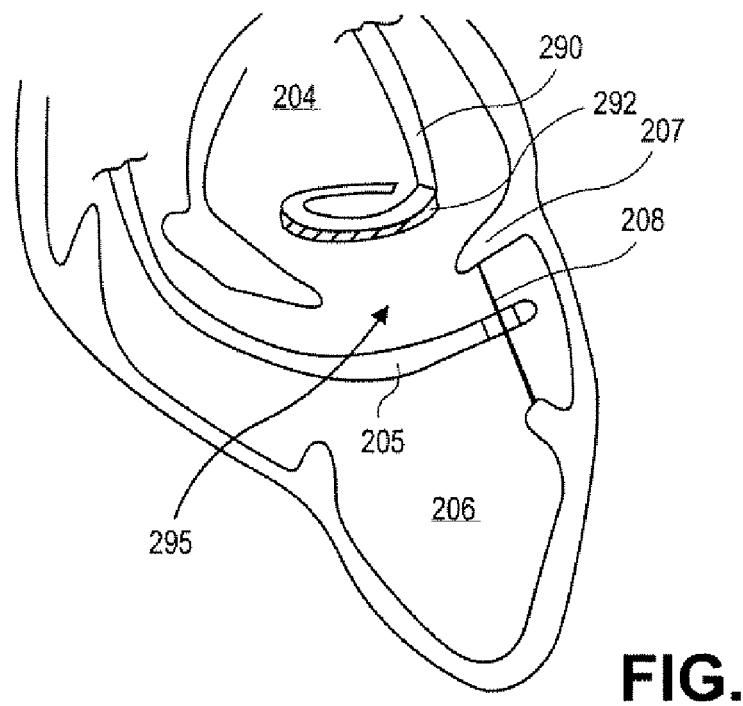
FIGS. 12A-12B illustrate one embodiment of performing a combination of percutaneous procedures.
Figure 12B:
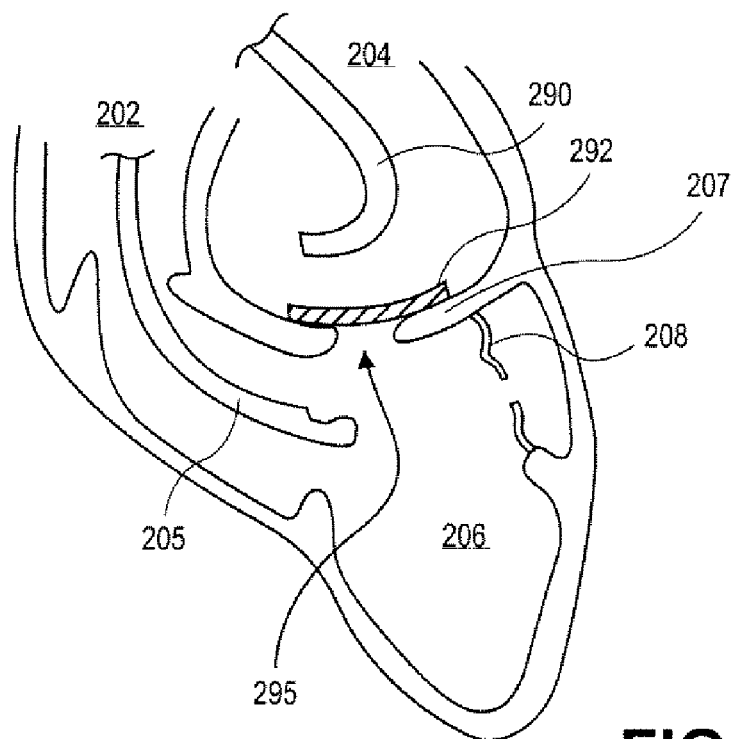

For example, FIGS. 12A-12B illustrate one embodiment of performing a combination procedure of percutaneous mitral valve chordae cutting with percutaneous placement of a support annulus on the mitral valve annulus. FIG. 12A shows a first catheter 205 having a cutting element disposed near a distal end and positioned near chordae 208 in left ventricle 206. A second catheter 290 has also been advanced percutaneously into the left atrium 204 (e.g., transeptally) and positioned over mitral valve annulus 295. A support member 292 is disposed near a distal portion of second catheter 290. FIG. 12B shows chordae 280 having been cut with a cutting element (e.g., cutting element 240 described above), as well as support member 290 having been attached to mitral valve annulus 295. Upon completion of each percutaneous procedure, first catheter 205 may be removed back up the aortic arch 202 and second catheter 290 may be removed back across the septum.

In the foregoing specification, a medical device has been described with reference to specific exemplary embodiments thereof. For example, the medical device may be used to treat heart chords other than the chordae tendineae of the mitral valve. It will, however, be evident that various modifications and changes may be made thereto without departing from the broader spirit and scope of the medical device as set forth in the appended claims. The specification and figures are, accordingly, to be regarded in an illustrative rather than a restrictive sense.

What is claimed is:

1. A medical device for percutaneous advancement to a heart chord, the medical device comprising:
    an elongated catheter having a proximal portion, a distal portion, and a notch formed near said distal portion; and
    a cutting element disposed within a groove in said notch and movable across said notch in said groove, wherein said cutting element is adapted to slice through said heart chord positioned within said notch.

2. The medical device of claim 1, further comprising a control mechanism disposed near said proximal portion of said elongated catheter.

3. The medical device of claim 2, wherein said cutting element comprises a blade having a first position distal to said notch and a second position proximal to said notch.

4. The medical device of claim 3, wherein said control mechanism retracts said blade from said first position to said second position.

5. The medical device of claim 2 further comprising a wire disposed within said elongated catheter, said wire coupling said control mechanism to said cutting element.

6. The medical device of claim 5, wherein said control mechanism moves said cutting element across said notch.

7. The medical device of claim 6, wherein said cutting element is adapted to slice through a mitral valve chordae.

8. The medical device of claim 7, wherein said notch is sized to receive said mitral valve chordae.

9. A medical device for percutaneously cutting a heart valve chord, the medical device comprising:
    an elongated catheter having a proximal portion, a distal portion, and a notch formed near said distal portion; and
    a retractable blade disposed within a groove in said notch, wherein said blade is moveable across said notch in said groove to slice through said heart valve chord when positioned within said notch.

10. The medical device of claim 9, further comprising a control mechanism disposed near said proximal portion.

11. The medical device of claim 10, further comprising a wire disposed within said elongated catheter and coupling said control mechanism to said retractable blade.

12. The medical device of claim 11, further comprising at least one steering tendon disposed within said elongated catheter and extending from said control mechanism to said distal portion.

13. The medical device of claim 12, wherein said blade comprises a metallic material.

14. The medical device of claim 12, wherein said notch has a depth of about 0.5 mm to 1.5 mm.

15. The medical device of claim 12, wherein said notch has a length of about 1 mm to 4 mm.

16. The medical device of claim 12, wherein said cutting element is adapted to slice through a mitral valve chordae.

17. An apparatus for cutting a heart valve chord, the apparatus comprising:
    means for advancing a cutting element disposed within a catheter to said heart valve chord percutaneously, said catheter having a notch formed therein;
    means for positioning said heart valve chord within said notch;
    means for actuating said cutting element across said notch to slice through said heart valve chord; and
    means for guiding said cutting element to slice through said heart valve chord in said notch.

18. The apparatus of claim 17, wherein means for actuating further comprises means for retracting said cutting element from a first position distal to said notch to a second position proximal to said notch.

19. The apparatus of claim 18, wherein means for actuating further comprises means for operating a control mechanism coupled to said cutting element.

20. The apparatus of claim 19, wherein means for positioning further comprises means for steering said catheter with said control mechanism.

21. The apparatus of claim 17, wherein means for advancing further comprises means for placing said catheter in a left ventricle of a patient's heart.

22. The apparatus of claim 21, wherein means for positioning further comprises means for placing a mitral valve chordae within said notch.

* * * * *